United States Patent
Claussner et al.

(10) Patent No.: US 6,242,611 B1
(45) Date of Patent: Jun. 5, 2001

(54) PHENYLIMIDAZOLIDINES CONTAINING NITROOXY OR CARBONYLOXY GROUPS

(75) Inventors: Andre Claussner, Villemomble; Francois Goubet, Paris; Jean-Georges Teutsch, Pantin, all of (FR)

(73) Assignee: Hoechst Marion Roussel (FR)

( * ) Notice: Subject to any disclaimer, the term of this patent is extended or adjusted under 35 U.S.C. 154(b) by 0 days.

(21) Appl. No.: 09/101,027

(22) PCT Filed: Dec. 19, 1996

(86) PCT No.: PCT/FR96/02029

§ 371 Date: Sep. 28, 1998

§ 102(e) Date: Sep. 28, 1998

(87) PCT Pub. No.: WO97/23464

PCT Pub. Date: Jul. 3, 1997

(30) Foreign Application Priority Data

Dec. 22, 1995 (FR) ................................... 95 15323

(51) Int. Cl.$^7$ .................. C07D 233/72; A61K 31/4166; A61N 5/28
(52) U.S. Cl. ................ 548/320.1; 514/398; 514/399; 514/400; 548/307.1; 548/319.1; 548/321.1
(58) Field of Search .............................. 548/307.1, 320.1; 514/398

(56) References Cited

U.S. PATENT DOCUMENTS 5,411,981 * 5/1995 Gaillard-Kelly et al. ........... 514/386
5,434,176 * 7/1995 Claussner et al. .................... 514/391
5,646,172 * 7/1997 Claussner et al. .................... 514/391

FOREIGN PATENT DOCUMENTS 2693461    1/1994  (FR).
9518794    7/1995  (WO).

* cited by examiner

Primary Examiner—Floyd D. Higel
(74) Attorney, Agent, or Firm—Bierman, Muserlian and Lucas

(57) ABSTRACT

A subject of the invention is the products of formula (I):

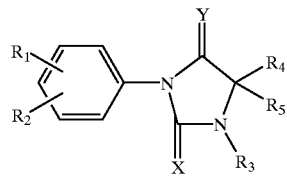

in which:

$R_1$ and $R_2$ represent in particular cyano and trifluoromethyl, $R_3$ represents in particular alkyl, alkenyl or alkynyl, substituted in particular by nitrooxy or carbonyloxy, $R_4$ and $R_5$ represent in particular methyl optionally substituted by fluorine, X and Y represent in particular oxygen, as well as their salts and isomers.

6 Claims, No Drawings

PHENYLIMIDAZOLIDINES CONTAINING NITROOXY OR CARBONYLOXY GROUPS

This application is a 371 of PCT/FR96/02029 filed Dec. 19, 1996.

The present invention relates to new phenylimidazolidines containing in particular a nitrooxy or carbonyloxy radical, their preparation process, the new intermediates obtained, their use as medicaments, their new use and the pharmaceutical compositions containing them.

A subject of the present invention is the products of formula (I):

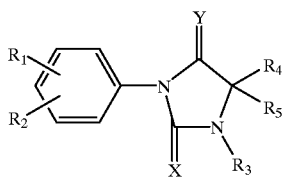

(I)

in which:
- $R_1$ and $R_2$, identical or different, are chosen from cyano, nitro, trifluoromethyl radicals and halogen atoms,
- $R_3$ represents a linear or branched aryl, arylalkyl, alkyl, alkenyl or alkynyl radical containing at most 10 carbon atoms substituted by a radical chosen from the following radicals: nitrooxy, alkoxycarbonyloxy, cycloalkoxycarbonyloxy, carboxyalkoxy, hydroxyacyl, hydroxyacyloxy, alkoxyacyl and alkoxyacyloxy, in which the alkyl, alkoxy, acyl and acyloxy radicals are linear or branched, containing at most 10 carbon atoms, the cycloalkoxy radical contains 3 to 7 members, the carboxy radical is free, salified, esterified or amidified and the hydroxy radical is free, esterified, etherified or protected,
- $R_4$ and $R_5$ are either identical or different and represent a linear or branched alkyl radical containing at most 4 carbon atoms and optionally substituted by a halogen atom, or form with the carbon atom to which they are linked a cyclic radical constituted by 3 to 7 members and optionally containing one or more identical or different heteroatoms, chosen from oxygen, sulphur or nitrogen atoms,
- X and Y, identical or different, represent an oxygen or sulphur atom, said products of formula (I) being in all the possible racemic, enantiomeric and diastereoisomeric isomer forms, as well as the addition salts with mineral and organic acids or with mineral and organic bases of said products of formula (I).

In the products of formula (I) and in what follows:
- the term halogen designates the fluorine, chlorine, bromine or iodine atoms.

The fluorine, chlorine or bromine atoms are preferred.

The term linear or branched alkyl radical designates the following radicals: methyl, ethyl, propyl, isopropyl, butyl, isobutyl, sec-butyl, tert-butyl, pentyl, isopentyl, hexyl, isohexyl and also heptyl, octyl, nonyl and decyl as well as their linear or branched position isomers.

The alkyl radicals having at most 6 carbon atoms are preferred and in particular the methyl, ethyl, propyl, isopropyl, n-butyl, n-pentyl and n-hexyl radicals, the term linear or branched alkenyl radical designates the vinyl, allyl, 1-propenyl, butenyl, 1-butenyl, pentenyl or hexenyl radical as well as their linear or branched position isomers.

Among the alkenyl radicals, the vinyl, allyl, n-butenyl or isobutenyl values are preferred, the term alkynyl designates a linear or branched radical having at most 12 and preferably 4 carbon atoms such as for example ethynyl, propargyl, butynyl, pentynyl or hexynyl.

Among the alkynyl radicals, the propargyl radical is preferred.

The term linear or branched alkoxy radical designates the following radicals: methoxy, ethoxy, propoxy, isopropoxy, linear, secondary or tertiary butoxy, pentoxy or hexoxy as well as their linear or branched position isomers, the term cyclic radical constituted by 3 to 7 members and optionally containing one or more identical or different heteroatoms, chosen from oxygen, sulphur or nitrogen atoms, designates on the one hand a cycloalkyl radical which itself designates in particular the cyclobutyl, cyclopentyl and cyclohexyl radicals and on the other hand a carbocyclic radical interrupted by one or more heteroatoms chosen from oxygen, nitrogen or sulphur atoms such as quite particularly the saturated monocyclic heterocyclic radicals. The following radicals can be mentioned for example: oxetannyl, oxolannyl, dioxanyl, dithiolane, thiooxolane, thiooxane, pyrrolidinyl, piperidyl, piperazinyl, morpholinyl, azetidine, oxetane and thietane, and there can be indicated quite particularly:

the rings with 4 members containing at most 1 heteroatom, such as:

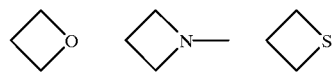

the rings with 5 members containing at most 1 heteroatom, such as:

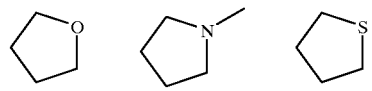

the rings with 6 members containing at most 6 heteroatoms, such as:

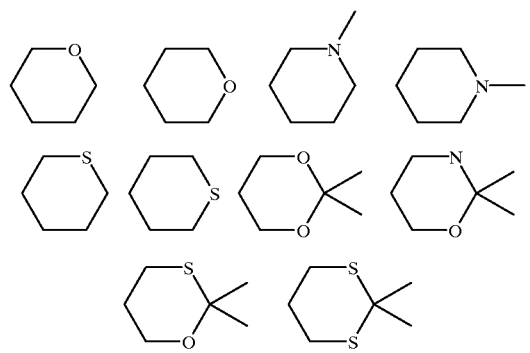

The following radical can also be indicated:

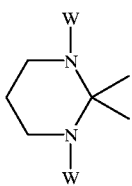

in which W represents an alkyl or aryl radical as defined above,
   the term cycloalkoxy radical represents in particular the cyclobutoxy, cyclopentoxy or cyclohexyloxy radicals,
   the term acyl radical preferably designates the formyl, acetyl, propionyl, butyryl and benzoyl radicals, but also the valeryl, hexanoyl, acryloyl, crotonoyl and carbamoyl radicals,
   the term acyloxy radical designates the radicals in which- the acyl radicals have the meaning indicated above and for example the acetoxy or propionyloxy radicals,
   the term aryl designates the carbocyclic aryl radicals such as phenyl or naphthyl and the monocyclic heterocyclic aryl radicals with 5 or 6 members or constituted by condensed rings, containing one or more heteroatoms preferably chosen from oxygen, sulphur and nitrogen. Among the heterocyclic aryls with 5 members, the following radicals can be mentioned: furyl, thienyl, pyrrolyl, thiazolyl, oxazolyl, imidazolyl, thiadiazolyl, pyrazolyl, isoxazolyl, tetrazolyl.

Among the heterocyclic aryls with 6 members, the pyridyl, pyrimidinyl, pyridazinyl, pyrazinyl radicals can be mentioned.

Among the condensed aryl radicals, the indolyl, benzofurannyl, benzothienyl, quinolinyl radicals can be mentioned. The phenyl, tetrazolyl and pyridyl radicals are preferred.

The term arylalkyl designates the radicals resulting from the combination of the alkyl radicals and the aryl radicals mentioned above.

The benzyl, phenylethyl, pyridylmethyl, pyridylethyl or tetrazolylmethyl radicals are preferred.
   the terms alkoxy- and cycloalkoxy-carbonyloxy, carboxyalkoxy, hydroxy- and alkoxy-acyl and -acyloxy, represent the radicals in which the alkoxy, acyl and acyloxy radicals have the meanings indicated above: there can be mentioned for example and in a non-expaustive manner, the following radicals: isopropyloxycarbonyloxy, cyclopentyloxycarbonyloxy, cyclohexyloxycarbonyloxy, methoxycarbonyloxy, carboxybutyl, ethoxycarbonylbutyl, hydroxyacetyl, hydroxypropionyl or methoxybutyryl; hydroxyacetoxy or hydroxypropionyloxy; methoxy- or ethoxypropionyloxy.

By way of example and in a non-exhaustive manner, in addition to the values indicated above and to those given hereafter, in particular in the experimental part, $R_3$ can therefore in particular represent the isopropyloxy- or cyclohexyloxy or cyclopentyloxy -carbonyloxybutyl or the corresponding radicals in which the isopropyloxy remainder and the butyl remainder take the other values of the alkoxy and alkyl radicals mentioned above respectively such as, for example, pentoxy, butoxy, ethoxy, pentyl or isopropyl; such alkyl radicals can also be replaced by alkenyl or alkynyl remainders such as for example pentenyl, butenyl, propenyl, pentynyl, butynyl or allyl or also by aryl or arylalkyl remainders as defined above, such as, for example, phenyl, pyridyl, benzyl, phenethyl, pyridylmethyl or pyridylethyl. $R_3$ can also represent for example the following radicals: hydroxymethylcarbonylethyl, hydroxymethylcarbonylmethyl, hydroxy-1-difluoro-2,2-butyl, hydroxy-1-difluoro-2,2-propyl, hydroxyphenylmethyl, dihydroxyphenylmethyl, hydroxyphenyl or also hydroxymethylphenyl.

As particular examples of an alkyl radical substituted by a halogen atom, there can be mentioned the mono-fluoro-, chloro- or bromo-methyl, ethyl and -isopropyl radicals.

The carboxy radical or radicals of the products of formula (I) can be free, salified, esterified or amidified by various groups known to a man skilled in the art, amongst which there can be mentioned, for example:
   among the salification compounds, mineral bases such as, for example, an equivalent of sodium, potassium, lithium, calcium, magnesium or ammonium or organic bases such as, for example, methylamine, propylamine, trimethylamine, diethylamine, triethylamine, N,N-dimethylethanolamine, tris (hydroxymethyl) amino methane, ethanolamine, pyridine, picoline, dicyclohexylamine, morpholine, benzylamine, procaine, lysine, arginine, histidine, N-methylglucamine.

The sodium or potassium salts are preferred.

Among the esterification compounds, the alkyl radicals in order to form alkoxy carbonyl groups such as, for example, methoxycarbonyl, ethoxycarbonyl, propoxycarbonyl, butoxy-, isobutoxy- and tert-butoxy-carbonyl or benzyloxycarbonyl, these alkyl radicals being able to be substituted by radicals chosen for example from halogen atoms, hydroxyl, alkoxy, acyl, acyloxy, alkylthio, amino or aryl radicals such as, for example, in the following groups: chloromethyl, hydroxypropyl, methoxymethyl, propionyloxymethyl, methylthiomethyl, dimethylaminoethyl, benzyl or phenethyl.

Radicals formed with the easily cleavable ester remainders can also be mentioned such as the methoxymethyl, ethoxymethyl radicals; the acyloxyalkyl radicals such as pivaloyloxymethyl, pivaloyloxyethyl, acetoxymethyl or acetoxyethyl; the alkyloxycarbonyloxy alkyl radicals such as the methoxycarbonyloxy methyl or ethyl radicals, the isopropyloxycarbonyl methyl or ethyl radicals.

A list of such ester radicals can be found for example in the European Patent EP 0,034,536.

By amidified carboxy is meant the groups of —CON($R_6$)($R_7$) type in which the R6 and $R_7$ radicals, identical or different, represent a hydrogen atom or an alkyl radical having 1 to 4 carbon atoms such as the methyl, ethyl, propyl, isopropyl, butyl, isobutyl, sec-butyl or tert-butyl radicals.

Among the —CON($R_6$)($R_7$) groups defined above, those in which the —N($R_6$)($R_7$) radical represents the amino, mono or dimethylamino radical are preferred.

The N($R_6$)($R_7$) radical can also represent a heterocycle which may or may not contain an additional heteroatom. The pyrrolyl, imidazolyl, indolyl, piperidinyl, morpholinyl, piperazinyl radicals can be mentioned. The piperidino or morpholino radicals are preferred.

Examples of the protective group of the protected hydroxyl radical are given in particular in the usual book of a man skilled in the art: Protective Groups in Organic Synthesis, Theodora W. Greene, Harvard University, published in 1981 by Wiley-Interscience Publishers, John Wiley & Sons.

The addition salts with mineral or organic acids of the products of formula (I) can be, for example, the salts formed with the following acids: hydrochloric, hydrobromic, hydroiodic, nitric, sulphuric, phosphoric, propionic, acetic, formic, benzoic, maleic, fumaric, succinic, tartaric, citric, oxalic, glyoxylic, aspartic, ascorbic, alkylmonosulphonic such as for example methanesulphonic, ethanesulphonic, propanesulphonic, alkyldisulphonic such as for example methanedisulphonic, alpha, beta-ethanedisulphonic, arylmonosulphonic such as benzenesulphonic, metasulphobenzoic and aryldisulphonic.

There can be mentioned more particularly the salts formed with hydrochloric or methanesulphonic acids for example.

It may be remembered that stereoisomerism can be defined as the isomerism of compounds having the same developed formulae, but the different groups of which are arranged differently in space, such as in particular in the boat and chair shapes of the cyclohexane and mono-substituted cyclohexanes whose substituent can be in the axial or equatorial position, and the different possible rotational conformations of ethane derivatives. However, another type of stereoisomerism exists, due to the different spatial arrangements of substituents fixed either on bond doubles, or on rings, which is often called geometrical isomerism or cistrans isomerism. The term stereoisomeric is used in the present Application in its broadest sense and therefore relates to all of the compounds indicated above.

In the products of formula (I) and in what follows, it can be noted that:

the hydrogen atoms which are contained by the optionally substituted alkyl or alkenyl radicals that $R_3$ can represent, can be deuterium atoms, the fluorine atoms which can be represented by the halogen atoms, can be an $^{18}F$ atom useful for the medical imagery. $R_3$ thus represents in particular a linear or branched phenyl, pyridyl, benzyl, phenethyl, pyridylalkyl, alkyl, alkenyl or alkynyl radical, containing at most 10 carbon atoms, and substituted by a radical chosen from the following radicals:

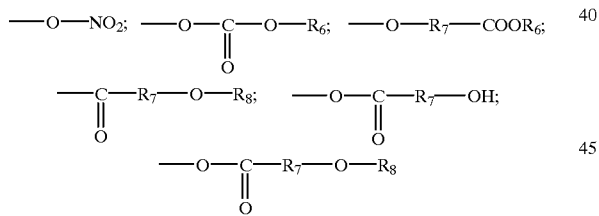

with $R_6$ representing a hydrogen atom, a linear or branched alkyl or acyl radical containing at most 6 carbon atoms or a cycloalkyl radical containing 3 to 7 members, and $R_7$ and $R_8$, identical or different, representing a linear or branched alkyl or acyl radical containing at most 6 carbon atoms.

Thus a subject of the present invention is the products of formula (I) as defined above, in which:

$R_1$ and $R_2$ either both represent a chlorine atom, or are identical or different and are chosen from cyano, nitro and trifluoromethyl radicals, $R_3$ represents a linear or branched phenyl, pyridyl, phenylalkyl, pyridylalkyl, alkyl, alkenyl or alkynyl radical containing at most 6 carbon atoms, substituted by a radical chosen from the following radicals: nitrooxy, hydroxyacyl, alkoxy-, acyloxy- and cycloalkoxy-carbonyloxy, in which radicals, if appropriate, the acyl, acyloxy and alkoxy radicals are linear or branched, containing at most 6 carbon atoms and the hydroxyl radical is free, esterified or protected, $R_4$ and $R_5$ are either identical or different and represent a methyl radical optionally substituted by a halogen atom, or form with the carbon atom to which they are linked a cyclobutyl, cyclopentyl, cyclohexyl, dioxanyl radical or a

radical in which W represents an oxygen, sulphur or —NH radical,

X and Y, identical or different, represent an oxygen or sulphur atom, said products of formula (I) being in all the possible racemic, enantiomeric and diastereoisomeric isomer forms, as well as the addition salts with mineral and organic acids or with mineral and organic bases of said products of formula (I).

The

radical represents in particular the piperidyl or tetrahydropyrannyl radical.

A particular subject of the present invention is the products of formula (I) as defined above, in which:

$R_1$ and $R_2$ represent a cyano radical and a trifluoromethyl radical, $R_3$ represents a linear or branched alkyl, alkenyl or alkynyl radical containing at most 4 carbon atoms substituted by a radical chosen from the nitrooxy and

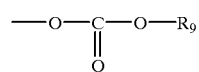

radicals in which $R_9$ represents a linear or branched alkyl radical containing at most 4 carbon atoms or a cycloalkyl radical containing 5 or 6 members, $R_4$ and $R_5$ are either identical or different and represent a methyl radical optionally substituted by a fluorine atom, or form with the carbon atom to which they are attached a cyclohexyl radical X and Y represent an oxygen atom, said products of formula (I) being in all the possible racemic, enantiomeric and diastereoisomeric isomer forms, as well as the addition salts with mineral and organic acids or with mineral and organic bases of said products of formula (I).

A particular subject of the present invention is the products of formula (I) as defined above in which $R_4$ and $R_5$ represent a methyl radical and $R_1$, $R_2$, $R_3$, X and Y have the meanings indicated above.

Among the preferred products of the invention, there can be mentioned more particularly the products of formula (I) as defined above the names of which follow:

4-(3-(4-cyano-3-(trifluoromethyl) phenyl)-5,5-dimethyl-2,4-dioxo-1-imidazolidinyl)butyl and 1-methylethyl carbonate, 4-(4,4-dimethyl-2,5-dioxo-3-(4-nitrooxybutyl)-1-imidazolidinyl)-2-(trifluoromethyl) benzonitrile, said products of formula (I) being in all the possible racemic, enantiomeric and diastereoisomeric isomer forms, as well as the addition salts with mineral and organic acids or with mineral and organic bases of said products of formula (I).

A subject of the present invention is also a preparation process for the products of formula (I), as defined above, characterized in that:

either, in the presence of a tertiary base, a product of formula (II):

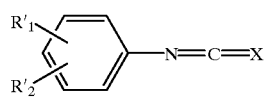

(II)

in which $R'_1$ and $R'_2$ have the meanings indicated above for $R_1$ and $R_2$ respectively, in which the optional reactive functions are optionally protected and X has the meaning indicated above, is reacted with a product of formula (III):

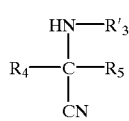

(III)

in which $R_4$ and $R_5$ have the meanings indicated above, and $R'_3$ has the meaning indicated above for $R_3$, in which the optional reactive functions are optionally protected, in order to obtain a product of formula (IV):

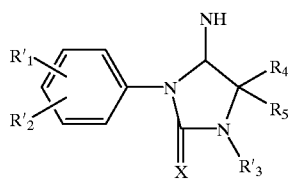

(IV)

in which X, $R'_1$, $R'_2$, $R'_3$, $R_4$ and $R_5$ have the meanings indicated above, which is converted into a product of formula (V):

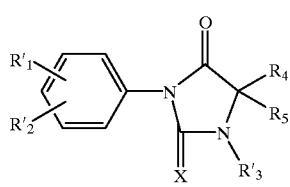

(V)

in which X, $R'_1$, $R'_2$, $R'_3$, $R_4$ and $R_5$ have the meanings indicated above, or a product of formula (VI):

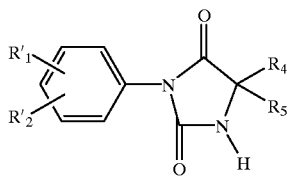

(VI)

in which $R'_1$, $R'_2$, $R_4$ and $R_5$ have the meanings indicated above, is reacted with a reagent of formula Hal-$R'_3$ in which $R'_3$ has the meaning indicated above, and Hal represents a halogen atom, in order to obtain the corresponding products of formula (V) as defined above in which X represents an oxygen atom, or is reacted on a product of formula (VII):

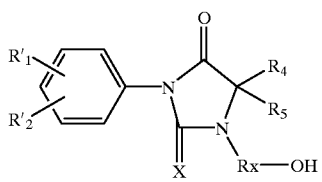

(VII)

in which $R'_1$, $R'_2$, $R_4$, $R_5$ and X have the meanings indicated above, and Rx represents a linear or branched aryl, arylalkyl, alkyl, alkenyl or alkynyl radical containing at most 10 carbon atoms, which is subjected:

either to the action of a compound of formula (VIII):

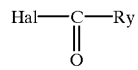

(VIII)

in which Hal represents a halogen atom and Ry represents a radical chosen from alkoxy, cycloalkoxy, hydroxyalkyl or alkoxyalkyl radicals, as defined above, in order to obtain a product of formula (IX):

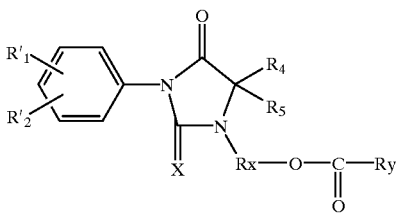

(IX)

in which $R'_1$, $R'_2$, $R_4$, $R_5$, X, Rx and Ry have the meanings indicated above, or to a halogenation reaction in order to obtain a product of formula (X):

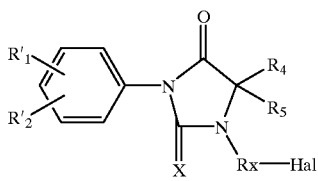

(X)

in which R'$_1$, R'$_2$, R$_4$, R$_5$, X, Rx and Hal have the meanings indicated above,
which is subjected to the action of silver nitrate in order to obtain the product of formula (XI):

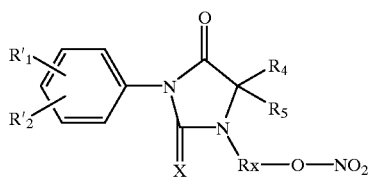

(XI)

in which R'$_1$, R'$_2$, R$_4$, R$_5$, X, Rx and Hal have the meanings indicated above,
which products of formulae (IV), (V), (IX) and (XI), if necessary or if desired, in order to obtain products of formula (I) as defined in claim 1, can be subjected to any one or more of the following reactions, in any order:
a) if appropriate conversion of the >C=S group which can be represented by >C=X into the >C=O group,
b) release of the OH radical which can be carried by R'$_3$,
c) esterification or etherification reaction of the OH radical which can be carried by R$_3$,
d) elimination reaction of the optional protective groups,
e) if appropriate the action of an esterification, amidification or salification agent,
f) resolution reaction of the racemic forms, said products of formula (I) thus obtained being in all the possible racemic, enantiomeric and diastereoisomeric isomer forms.

The action of the products of formula (II) with the products of formula (III) to obtain the products of formula (IV) can be carried out in the presence of methylene chloride, at a temperature of approximately −30° C., or also in an organic solvent such as tetrahydrofuran or dichloroethane, but ethyl ether or isopropyl ether can also be used.

The operation is carried out in the presence of a tertiary base such as triethylamine or also pyridine or methylethylpyridine.

The optional reactive functions which are optionally protected, can be in particular the hydroxy functions. To protect these functions standard protective groups are used such as indicated above. For example the following radicals can be mentioned in a non-exhaustive manner: tetrahydropyrannyl, trimethylsilyl, triphenylmethyl or tert-butyl dimethylsilyl or also the protective groups known in the chemistry of the peptides as indicated for example in the French Patent BF 2,499,995 whose content is incorporated here by reference.

In the product of formula (III), R$_4$ and R$_5$ can form a cyclic radical with the carbon atom which carries them such as in particular a cyclohexyl radical.

The optional elimination reactions of the protective groups are carried out according to the usual methods known to a man skilled in the art or, for example, as indicated in the Patent BF 2,499,995. The preferred method of elimination is acid hydrolysis using acids chosen from hydrochloric, benzene sulphonic or para toluene sulphonic, formic or trifluoroacetic acid. Hydrochloric acid is preferred.

The optional hydrolysis reaction of the >C=NH group into the carbonyl group in order to convert in particular the product of formula (IV) into the product of formula (V) is preferably carried out using an acid such as aqueous hydrochloric acid, for example under reflux.

The action on the products of formula (VI) of the reagent of formula Hal-R'$_3$ in order to obtain the products of formula (V) is carried out in the presence of a strong base such as sodium or potassium hydride. The operation can be carried out by phase transfer reaction in the presence of quaternary ammonium salts such as tetrabutyl ammonium dihydrogenphosphate salts.

The conversion of the OH radical into a halogen radical of the products of formula (VII) in order to obtain the products of formula (X) can be carried out under the usual conditions known to a man skilled in the art such as in particular in a solvent such as for example tetrahydrofuran and the action of a halogenated derivative such as in particular, when the halogen atom is a fluorine atom, diethylaminotrifluorosulphide (DAST).

Triflic anhydride can also be reacted beforehand in order to obtain the corresponding triflate which is then exchanged with the corresponding fluoride as is described hereafter in the examples and in particular by the action of tetrabutylammonium fluoride.

When the halogen atom is a bromine, chlorine or iodine atom, the operation can be carried out according to the usual conditions known to a man skilled in the art such as in particular by the action, in the presence of triphenylphosphine, of the corresponding halogenating agent such as for example carbon tetrabromide, carbon tetrachloride or also iodine.

Conversion reactions of the OH radical of the product of formula (VII) in order to obtain the products of formulae (IX) and (XI) as defined above in which R$_3$ has the meaning indicated above, are given, by way of example and in a non-exhaustive manner, in the preparations of Examples 1 to 4 described hereafter.

The optional esterification of the free OH radical is carried out under standard conditions. An acid or a functional derivative can for example be used, for example an anhydride such as acetic anhydride in the presence of a base such as pyridine.

The optional esterification, salification or amidification of the COOH radical is carried out under standard conditions known to a man skilled in the art such as, for example, for amidification, the use of a primary or secondary amine on a functional derivative of the acid for example a symmetrical or mixed anhydride.

Also a subject of the present invention is a preparation process for the products of formula (I'):

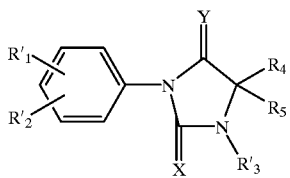

(I')

in which X, Y, R'$_1$, R'$_2$, R'$_3$, R$_4$ and R$_5$ are as defined above, process characterized in that a product of formula (P1):

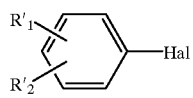

(P1)

in which R'$_1$ and R'$_2$ have the previous meanings and Hal represents a halogen atom, is reacted with a product of formula (P2):

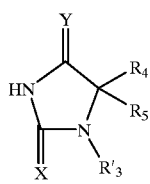

(P2)

in which X, Y, R'$_3$, R$_4$ and R$_5$ have the meanings indicated above, the reaction being carried out in the presence of a catalyst and optionally of a solvent.

With regard to the products of formula (P2), the term Hal preferably designates the chlorine atom, but can also represent a bromine or iodine atom.

The reaction conditions of such a process are in particular those described in EP 0494819.

The products which are a subject of the present invention have useful pharmacological properties, in particular they fix on the androgen receptors and'they present an anti-androgen activity.

Tests given in the experimental part illustrate these properties.

These properties make the products of formula (I) as defined above of the present invention of use as medicaments mainly for:

the treatment of adenomas and neoplasias of the prostate as well as benign hypertrophy of the prostate, on its own or in combination with analogues of LHRH. They can also be used in the treatment of benign or malignant tumours possessing androgen receptors and more particularly cancers of the breast, the skin, the ovaries, the bladder, the lymphatic system, the kidney and the liver, the treatment of cutaneous affections such as acne, hyperseborrhea, alopecia or hirsutism. These products can therefore be used on their own in dermatology or in combination with antibiotics such as the derivatives of azelaic and fusidic acids, erythromycin, as well as derivatives of retinoic acid or an inhibitor of 5 alpha-reductase such as (5 alpha,17 beta)-1,1-dimethylethyl 3-oxo 4-aza-androst-1-ene 17-carboxamide (or Finasteride, Merck 11th Ed.) for the treatment of acne, alopecia or hirsutism. They can also be combined with a product stimulating hair growth such as Minoxidil for the treatment of alopecia.

The products of formula (I), as defined above, in radio-active form (tritium, carbon 14, iodine 125 or fluorine 18) can also be used as specific labels for the androgen receptors. They can also be used in diagnostics using medical imagery.

The products of formula (I) as defined above can also be used in the veterinary domain for the treatment of behavioural disorders such as aggressiveness, androgen-dependent affections, such as circum analum in dogs and tumours having androgen receptors. They can also be used to bring about a chemical castration in animals.

Therefore a subject of the invention is the use, as medicaments, of the products of formula (I) as defined above, said products of formula (I) being in all the possible racemic or optically-active isomer forms, as well as the addition salts with pharmaceutically acceptable mineral or organic acids or mineral and organic bases of said products of formula (I).

A particular subject of the invention is the products of formula (I) as defined above, in which:

R$_1$ and R$_2$ represent a cyano radical and a trifluoromethyl radical,

R$_3$ represents a linear or branched alkyl, alkenyl or alkynyl radical containing at most 4 carbon atoms substituted by a radical chosen from the nitrooxo and

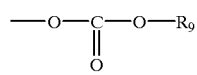

radicals in which R$_9$ represents a hydrogen atom, a linear or branched alkyl radical containing at most 4 carbon atoms or a cycloalkyl radical containing 5 or 6 members, R$_4$ and R$_5$ either are identical or different and represent a methyl radical optionally substituted by a fluorine atom, or form with the carbon atom to which they are attached a cyclohexyl radical X and Y represent an oxygen atom, said products of formula (I) being in all the possible racemic, enantiomeric and diastereoisomeric isomer forms, as well as the addition salts with pharmaceutically acceptable mineral and organic acids or mineral and organic bases of said products of formula (I).

A subject of the invention is also the use, as medicaments, of the following products:

4-(3-(4-cyano-3-(trifluoromethyl) phenyl)-5,5-dimethyl-2,4-dioxo-1-imidazolidinyl)butyl and 1-methylethyl carbonate, 4-(4,4-dimethyl-2,5-dioxo-3-(4-nitrooxybutyl)-1-imidazolidinyl)-2-(trifluoromethyl)benzonitrile, said products of formula (I) being in all the possible racemic, enantiomeric and diastereoisomeric isomer forms, as well as the addition salts with pharmaceutically acceptable mineral and organic acids or mineral and organic bases of said products of formula (I).

The products can be administered by parenteral, buccal, perlingual, rectal or topical route.

A subject of the invention is also the pharmaceutical compositions, characterized in that they contain, as active ingredient, at least one of the medicaments of formula (I), as defined above.

These compositions can be presented in the form of injectable solutions or suspensions, tablets, coated tablets, capsules, syrups, suppositories, creams, ointments and lotions. These pharmaceutical forms are prepared according to the usual methods. The active ingredient can be incorporated with excipients usually employed in these compositions, such as aqueous or non-aqueous vehicles, talc, gum arabic, lactose, starch, magnesium stearate, cocoa butter, fatty substances of animal or vegetable origin, paraffin derivatives, glycols, various wetting, dispersing or emulsifying agents, preservatives.

The usual dose, variable according to the subject treated and the affection in question, can be, for example, from 10 mg to 500 mg per day for man, by oral route.

The products of formula (II) used at the start of the invention can be obtained by the action of phosgene when X represents an oxygen atom or thiophosgene when X represents a sulphur atom on the corresponding amine of formula (A):

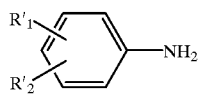

(A)

in which $R'_1$ and $R'_2$ have the meanings indicated above.

A product of this type is described in particular in the French Patent BF 2,329,276.

Amines of formula (A) are described in the European Patent EP 0,002,892 or the French Patent BF 2,142,804.

The products of formula (III) are known or can be prepared from the corresponding cyanhydrin according to the process described in the publications: J. Am. Chem. Soc. (1953), 75, 4841, BEIL I 4 526 or J. Org. Chem. 27 2901 (1962).

The products of formula (III) can also be obtained by the action of a product of formula $R'_3$ Hal on 2-cyano 2-amino propane. A preparation example of this type is described in the reference:

Jilek et al. Collect. Czech. Chem. Comm. 54(8) 2248 (1989).

The starting products of formulae (P1), (P2) and (VIII) as defined above are known and commercially available or can be prepared according to the methods known to a man skilled in the art.

The compound of formula (VIII) can in particular be an alkyl or cycloalkyl chloroformate, as is indicated in the preparation of Examples 1 to 3.

The preparation of products of formula (P2) is described in particular in the following publications:

Zhur. Preklad. Khim. 28, 969-75 (1955) (CA 50, 4881a, 1956)

Tetrahedron 43, 1753 (1987)

J. Org. Chem. 52, 2407 (1987)

Zh. Org. Khim. 21, 2006 (1985)

J. Fluor. Chem. 17, 345 (1981)

or in the Patents:

German DRP 637,318 (1935)

European EP 0,130,875

Japanese JP 81,121,524.

The products of formula (P2) which are derivatives of hydantoin are widely used and mentioned in the literature such as for example in the following articles:

J. Pharm. Pharmacol., 67, Vol. 19(4), p. 209–16 (1967)

Khim. Farm. Zh., 67, Vol. 1 (5) p. 51–2

German Patent 2,217,914

European Patent 0,091,596

J. Chem. Soc. Perkin. Trans. 1, p. 219–21 (1974).

The starting products of formulae (VI) and (VII) can be prepared in particular as indicated in the Patent Applications EP 0494819 or EP 0580459.

A subject of the invention is also, as new industrial products and in particular as new industrial products of use as intermediates for the preparation of products of formula (I) as defined above, the products of formulae (IV) and (V) as defined above.

A subject of the present invention is also the use of the products of formula (I) as defined above, for the preparation of pharmaceutical compositions intended for the treatment of adenomas and neoplasias of the prostate as well as of benign hypertrophy of the prostate, on their own or in combination with analogues of LHRH, for the treatment of cutaneous affections such as acne, hyperseborrhea, alopecia or hirsutism or in diagnostics using medical imagery.

A particular subject of the present invention is the use of the products of formula (I) as defined above, in which $R_3$ represents a radical substituted by the nitrooxy radical, for the preparation of pharmaceutical compositions intended for the treatment of cutaneous affections such as acne, alopecia or hirsutism.

The following examples illustrate the invention without however limiting it.

EXAMPLE 1

4-(3-(4-cyano-3-(trifluoromethyl)-phenyl)-5,5-dimethyl-2,4-dioxo-1-imidazolidinyl)butyl and 1-methylethyl carbonate 0.369 g of 4-(4,4-dimethyl-2,5-dioxo-3-(4-hydroxybutyl)-1-imidazolidinyl)-2-(trifluoromethyl)-benzonitrile obtained in Example 1 of EP 0,580,459 and 24 ml of dimethylaminopyridine in solution in 3.5 mg of pyridine dried over potash are introduced, the whole is cooled down to 0° C. and 2 ml of a toluenic solution of 1 M isopropyl chloroformate is added. After 2 hours 15 minutes of agitation, the reaction medium is poured into 30 g of water+ice and extracted with ether. The ethereal phases are combined, washed with a saturated solution of sodium chloride and dried. The oil obtained is taken up in toluene and evaporation to dryness is carried out under reduced pressure. After chromatography on silica, eluting with methylene chloride—ethyl acetate: 100-3, 0.413 g of expected product (white crystals) is obtained. M.p.=82° C.

ANALYSES

Microanalysis for $C_{21}H_{24}F_3N_3O_5$: 455.44

|  | C % | H % | F % | N % |
|---|---|---|---|---|
| calculated | 55.38 | 5.31 | 12.51 | 9.23 |
| found | 55.4 | 5.2 | 12.7 | 9.2 |

EXAMPLE 2

4-[3-[4-cyano-3-(trifluoromethyl) phenyl]-5,5-dimethyl-2,4-dioxo-1-imidazolidinyl] butyl and cyclohexyl carbonate The operation is carried out as in Example 1, starting with 740 mg of 4-(4,4-dimethyl-2,5-dioxo-3-(4-hydroxybutyl)-1- imidazolidinyl)-2-(trifluoromethyl)-benzonitrile obtained in Example 1 of EP 0,580,459, 48 mg of 4-dimethylaminopyridine and 7 ml of pyridine, the whole is cooled down to 10° C.±2° C. and 650 mg of cyclohexyl chloroformate is added. The operation is continued as in Example 1 and after chromatography on silica, eluting with methylene chloride—ethyl acetate: 97-3, 948 mg of expected product is obtained.

M.p.=121–122° C.

ANALYSES

Microanalysis for $C_{24}H_{28}F_3N_3O_5$: 495.5

|  | C % | H % | F % | N % |
|---|---|---|---|---|
| calculated | 58.18 | 5.70 | 11.50 | 8.48 |
| found | 58.2 | 5.8 | 11.3 | 8.4 |

EXAMPLE 3

4-[3-[4-cyano-3-(trifluoromethyl) phenyl]-5,5-dimethyl-2,4-dioxo-1-imidazolidinyl] butyl and cyclopentyl carbonate The operation is carried out as in Example 2, starting with 740 mg of 4-(4,4-dimethyl-2,5-dioxo-3-(4-hydroxybutyl)-1-imidazolidinyl)-2-(trifluoromethyl)-benzonitrile obtained in Example 1 of EP 0,580,459, 48 mg of 4-dimethylaminopyridine and 7 ml of pyridine, the whole is cooled down in an ice bath and 600 mg of cyclopentyl chloroformate is added. By proceeding as in Example 2, 904 mg of expected product (white crystals) is obtained. M.p.= 81–82° C.

ANALYSES

Microanalysis for $C_{23}H_{26}F_3N_3O_5$: 481.47

|  | C % | H % | F % | N % |
|---|---|---|---|---|
| calculated | 57.37 | 5.44 | 11.84 | 8.73 |
| found | 57.5 | 5.4 | 11.7 | 8.7 |

EXAMPLE 4

4-(4,4-dimethyl-2,5-dioxo-3-(4-nitrooxybutyl)-1 imidazolidinyl)-2-(trifluoromethyl)-benzonitrile STAGE 1: 4-(4,4-dimethyl-2,5-dioxo-3-(4-iodobutyl)-1-imidazolidinyl)-2-(trifluoromethyl)-benzonitrile 787 mg of triphenyl phosphine, 204 mg of imidazole, 762 mg of iodine and 5 ml of methylene chloride are introduced, the suspension is agitated for 45 minutes at ambient temperature, then over about 3 minutes, 1.1 g of 4-( 4,4-dimethyl-2,5-dioxo-3-(4-hydroxybutyl)-1-imidazolidinyl)-2-(trifluoromethyl)-benzonitrile obtained in Example 1 of EP 0,580,459 in 7 ml of methylene chloride is added. Rinsing is carried out with 1 ml of methylene chloride followed by agitation for 4 hours at ambient temperature.

The insoluble part is separated off, rinsed with methylene chloride, the organic phase is washed with a saturated aqueous solution of sodium thiosulphate then with salt water and dried. Chromatography is carried out on silica eluting with methylene chloride—ethyl acetate: 97-3. After crystal-lization from ether, 1.26 g of expected product (white crystals) is obtained. M.p.=87–88° C.

Physical Analyses

Microanalysis for $C_{17}H_{17}F_3IN_3O_2$: 479.24

|  | C % | H % | F % | I % | N % |
|---|---|---|---|---|---|
| calculated | 42.61 | 3.57 | 11.89 | 26.48 | 8.77 |
| found | 42.7 | 3.3 | 11.9 | 26.2 | 8.5 |

STAGE 2: 4-(4,4-dimethyl-2,5-dioxo-3-(4-nitrooxybutyl)-1imidazolidinyl)-2-(trifluoromethyl)-benzonitrile 1 g of the product obtained in Stage 1 above, is introduced into 10 ml of acetonitrile and 426 mg of silver nitrate is added to the solution obtained. The reaction medium is left to react 16 hours at ambient temperature, the insoluble part is separated off, rinsed twice with methylene chloride and evaporated. After purification by chromatography on silica eluting with methylene chloride—ethyl acetate: 99-1, 845 mg of expected product (white crystals) is obtained. M.p.= 74–75° C.

Physical Analyses

Microanalysis for $C_{17}H_{17}F_3N_4O_5$: 414.34

|  | C % | H % | F % | N % |
|---|---|---|---|---|
| calculated | 49.28 | 4.13 | 13.75 | 13.52 |
| found | 49.2 | 4.0 | 13.7 | 13.5 |

EXAMPLE 5

Tablets were prepared having the following composition:
Product of Example 1 . . . 100 mg
Excipient s.q. for a tablet made up to . . . 300 mg
(Detail of the excipient: lactose, starch, talc, magnesium stearate).

PHARMACOLOGICAL STUDY OF THE PRODUCTS OF THE INVENTION

1) Study of the Affinity of the Products of the Invention for the Androgen Receptor Male Sprague Dawley EOPS rats weighing 180–200 g, castrated 24 hours previously, are sacrificed, the prostates are removed, weighed and homogenized at 0° C. using a potter glass flask, in a buffered solution (10 mM Tris, 0.25M saccharose, 0.1 mM PMSF (phenylmethanesulphonylfluoride), 20 mM sodium molybdate, HCl pH 7.4; to which 2 mM of DTT (DL dithiothreitol) is added extemporaneously), at the rate of 1 g of tissue per 8 ml of buffer.

The homogenate is then ultracentrifuged at 0° C., for 30 minutes at 209,000 g. The aliquots of the supernatant obtained (=cytosol), are incubated for 30 minutes and for 24 hours at 0° C., with a constant concentration (T) of tritiated testosterone and in the presence of increasing concentrations (0 to $2500\times10^{-9}$M), either of unlabelled testosterone, or of the products to be tested. The concentration of bound tritiated testosterone (B) is then measured in each incubate by the method of adsorption on carbon-dextran.

Calculation of the Relative Bond Affinity (RBA)

The following 2 curves are drawn: the percentage of the bound tritiated hormone B/T as a function of the logarithm of the concentration of the unlabelled reference hormone and B/T as a function of the logarithm of the concentration of unlabelled tested product. The straight line of the equation $I_{50}=(B/Tmax+B/Tmin)/2$.

B/T max=of the bound tritiated hormone for an incubation of this tritiated hormone at the concentration (T).

B/T min=% of the bound tritiated hormone for an incubation of this tritiated hormone at the concentration (T) in the presence of a large excess of unlabelled hormone $(2500 \times 10^{-9} M)$.

The intersections of the straight line $I_{50}$ and the curves, allow the evaluation of the concentrations of theunlabelled reference hormone (CH) and of the tested unlabelled product (CX) which inhibit by 50% the bindingof the tritiated hormone on the receptor. The relative bond affinity (RBA) of the tested product is determined by the equation RBA=100 (CH)/(CX).

The following results are obtained, expressed in RBA.
Reference product (testosterone): 100

TABLE 1

| Product of example | RBA: Incubation for 24 hours |
|---|---|
| 1 | 19 |

2) Determination of the Reducing Effect on the Costo-vertebral Gland of the Hamster The local activity (topical) of an antiandrogen is determined by the reduction which it produces in the surface area of the costovertebral gland of the hamster (hereafter C.V.G.), an androgen-dependent organ situated on the sides of the animal.

The animals are male hamsters weighing approximately 140 g, 14 weeks old and originating from the Charles Riverbreed (USA), they are subjected to a long photoperiod (16 hours of light, 8 hours of darkness). The animals are treated every day, except for the weekend, for 3 weeks (14 administrations). The product to be tested is applied, by topical route, to the right-hand G.C.V., the left-hand one serving as the control, the surface of the gland having been shaved beforehand. The animals are sacrificed by bleeding the carotid artery 24 hours after the last treatment. The C.V.G.'s are removed, measured and weighed. The local activity of a product is determined by the % reduction in the surface area of the C.V.G. which it induces in comparison with the 1st of day the experiment and compared to the animals treated with solvent only.

TABLE 2

| Product of example | % CVG reduction with 3 µg/jour |
|---|---|
| 1 | -32 |

3) Determination of the Reducing Effect in the Weight of the Prostate in an Intact Male Rat The systemic activity of an antiandrogen is determined by the reduction in the weight of the prostate which it produces in an intact animal.

The animals used are male rats of the Sprague Dawley strain weighing approximately 200 g, 7 weeks old, originating from the Iffa Credo breed (France). The experiment is carried out over two weeks, except for the weekend.

The product can be administered by oral, sub-cutaneous or percutaneous route.

The solvents used are then:

by oral route: 0.5% aqueous solution of methylcellulose under a volume of 5 ml/kg, by sub-cutaneous route: wheatgerm oil in 10% ethanol under a volume of 0.2 ml/kg, and by percutaneous route: ethanol under a volume of 50 µl on the previously-shaved skin.

The treatment is carried out from day 0 to day 4 then (after the weekend) from day 7 to day 10. The animals are sacrificed the day after the last treatment by bleeding the carotid artery, the prostates are removed and fixed in demineralized water containing 10% formol for 72 hours. They are then dissected and weighed. The blood is removed in order to determine, by radioimmunological assay, the amount of seric testosterone. The anti-androgen activity of the product is expressed in % reduction in the weight of the prostates and in % variation in the amounts of testosterone compared to the animals treated with the solvent only.

TABLE 3

| Product of example | % réduction in the prostate weight with 3 mg/kg P.O. |
|---|---|
| 1 | -5 |

What is claimed is:

1. A compound selected from the group consisting of a compound of the formula

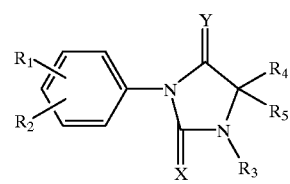

wherein $R_1$ and $R_2$ are individually selected from the group consisting of —CN, and —CF$_3$, $R_3$ is selected from the group consisting of alkyl, alkenyl and alkynyl, all of up to 4 carbon atoms and substituted with a member selected from the group consisting of nitrooxy and

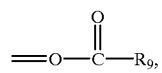

$R_9$ is alkoxy of 1 to 4 carbon atoms or cycloalkyloxy of 5 to 6 carbon atoms, $R_4$ and $R_5$ are individually methyl unsubstituted or substituted by fluorine or taken together with the carbon atom to which they are attached form cyclohexyl, X and Y are oxygen in all racemic, enantiomeric and diasostereo isomeric forms thereof and its salts of a non-toxic, pharmaceutically acceptable base and acid.

2. A compound having the formula

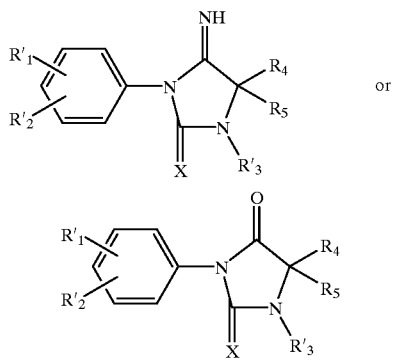

or

X is oxygen or sulfur, $R'_1$, $R'_2$, $R'_3$ and $R'_4$ have the definition of $R_1$, $R_2$, $R_3$ and $R_4$ in claim 1 with any reactive groups unprotected or protected and $R_4$ and $R_5$ are as defined in claim 1.

3. An antiandrogenic composition comprising an antiandrogenically effective amount of a compound selected from the group consisting of 4-(3-(4-cyano-3-trifluoromethyl-phenyl)-5,5-dimethyl-2,4-dioxo-1-imidazolidinyl)-butyl and isopropyl carbonate and 4-(4,4-dimethyl-2,5-dioxo-3-(4-nitrooxybutyl)-1-imidazolidinyl-2-trifluoromethyl-benzonitrile.

4. A compound of claim 1 selected from the group consisting of
   4-(3-(4-cyano-3-(trifluoromethyl) phenyl)-5,5-dimethyl-2,4-dioxo-1-imidazolidinyl)butyl and 1-methylethyl carbonate,
   4-(4,4-dimethyl-2,5-dioxo-3-(4-nitrooxybutyl)-1 imidazolidinyl)-2-(trifluoromethyl) benzonitrile,
said products of formula (I) being in all the possible racemic, enantiomeric and diastereoisomeric isomer forms, or the addition salts with mineral and organic acids or with mineral and organic bases of said products of formula (I).

5. A method of inducing antiandrogenic activity in a warm blooded animal comprising administering to warm-blooded animals an antiandrogenically effective amount of a compound of claim 1.

6. The method of claim 5, wherein the compound is selected from the group consisting of
   4-(3-(4-cyano-3-(trifluoromethyl) phenyl)-5,5-dimethyl-2,4-dioxo-1-imidazolidinyl)butyl and 1-methylethyl carbonate,
   4-(4,4-dimethyl-2,5-dioxo-3-(4-nitrooxybutyl)-1 imidazolidinyl)-2-(trifluoromethyl) benzonitrile.

* * * * *